(12) United States Patent
Dohi (10) Patent No.: US 8,638,436 B2
(45) Date of Patent: Jan. 28, 2014

(54) SMOKE SENSOR

(75) Inventor: Manabu Dohi, Tokyo (JP)

(73) Assignee: Hochiki Corporation (JP)

( * ) Notice: Subject to any disclaimer, the term of this patent is extended or adjusted under 35 U.S.C. 154(b) by 0 days.

(21) Appl. No.: 13/395,626

(22) PCT Filed: Sep. 15, 2009

(86) PCT No.: PCT/JP2009/004602
§ 371 (c)(1),
(2), (4) Date: Mar. 12, 2012

(87) PCT Pub. No.: WO2011/033552
PCT Pub. Date: Mar. 24, 2011

(65) Prior Publication Data
US 2012/0170035 A1    Jul. 5, 2012

(51) Int. Cl.
*G01N 21/49* (2006.01)
*G08B 21/00* (2006.01)

(52) U.S. Cl.
USPC ........... 356/343; 356/437; 356/438; 340/630; 340/628

(58) Field of Classification Search
USPC .......... 356/432–444, 336–343; 250/216, 574; 340/630, 628, 629, 577
See application file for complete search history.

(56) References Cited

U.S. PATENT DOCUMENTS

| 5,280,272 | A |   | 1/1994  | Nagashima et al. |
|---|---|---|---|---|
| 5,477,218 | A | * | 12/1995 | Manmoto et al. ............. 340/630 |
| 5,502,434 | A | * | 3/1996  | Minowa et al. ............... 340/630 |
| 5,576,697 | A |   | 11/1996 | Nagashima et al. |
| 6,967,582 | B2 | * | 11/2005 | Tice et al. ..................... 340/630 |
| 8,232,885 | B2 | * | 7/2012  | Hoshino et al. ............... 340/630 |

(Continued)

FOREIGN PATENT DOCUMENTS

| CN | 1882968A A | 12/2006 |
|---|---|---|
| EP | 0877345 A2 | 11/1998 |

(Continued)

*Primary Examiner* — Sang Nguyen
(74) *Attorney, Agent, or Firm* — Blank Rome LLP (57) ABSTRACT

[Problem to be Solved]
To provide a smoke sensing system, a smoke sensor and a receiver that can accurately determine the type of smoke.
[Solution]
The smoke sensor includes: a light-projecting unit 13 for projecting detection light toward a monitored area; a first light-receiving unit 14a, a second light-receiving unit 14b and a third light-receiving unit 14c for receiving the detection light scattered by particles existing in the monitored area, the first light-receiving unit 14a, the second light-receiving unit 14b and the third light-receiving unit 14c being arranged such that the angle between the light-receiving axis of the first light-receiving unit 14a and the light-projecting axis of the light-projecting unit 13, the angle between the light-receiving axis of the second light-receiving unit 14b and the light-projecting axis of the light-projecting unit 13 and the angle between the light-receiving axis of the third light-receiving unit 14c and the light-projecting axis of the light-projecting unit 13 are different from one another; a smoke type determination unit 47 for determining the type of smoke generated in the monitored area based on the output values output from the first light-receiving unit 14a, the second light-receiving unit 14b and the third light-receiving unit 14c; and a fire determination unit 48 for determining whether or not a fire has occurred in the monitored area based on the output values output from the first light-receiving unit 14a, the second light-receiving unit 14b and the third light-receiving unit 14c.

12 Claims, 7 Drawing Sheets

(56) References Cited

U.S. PATENT DOCUMENTS

| | | | |
|---|---|---|---|
| 8,253,578 B2 * | 8/2012 | Watabe et al. | 340/628 |
| 2008/0246623 A1 * | 10/2008 | Nagashima | 340/630 |
| 2008/0258925 A1 | 10/2008 | Siber et al. | |
| 2009/0026354 A1 * | 1/2009 | Nakajima et al. | 250/216 |
| 2010/0118303 A1 | 5/2010 | Nagashima | |

FOREIGN PATENT DOCUMENTS

| | | |
|---|---|---|
| EP | 1688898 A1 | 8/2006 |
| JP | 99290/1982 | 12/1980 |
| JP | 3042800 A | 2/1991 |
| JP | H04-205400 | 7/1992 |
| JP | 4299499 A | 10/1992 |
| JP | 5081578 A | 4/1993 |
| JP | 6109631 A | 4/1994 |
| JP | H06-109631 | 4/1994 |
| JP | 11023458 A | 1/1999 |
| JP | 2004325211 A | 11/2004 |
| JP | 4124798 B2 | 7/2008 |
| JP | 04-205400 B2 | 1/2009 |
| WO | 2005048208 A1 | 5/2005 |

* cited by examiner

|  | 50°/40° | 150°/50° | 150°/40° |
|---|---|---|---|
| WOOD BURNING | 0.70 | 0.65 | 0.45 |
| WOOD SMOKING | 0.60 | 0.45 | 0.30 |
| DUST (FLY ASH) | 0.80 | 0.80 | 0.60 |

SMOKE SENSOR

REFERENCE TO RELATED APPLICATION

The present application is the U.S. national phase of PCT International Patent Application No. PCT/JP2009/004602, filed Sep. 15, 2009, published on Mar. 24, 2011, as WO 2011/033552 A1, the entire disclosures of which are incorporated herein by reference.

TECHNICAL FIELD

The present invention relates to a smoke sensing system, a smoke sensor and a receiver for detecting the occurrence of a fire by sensing smoke.

BACKGROUND ART

Conventionally, various smoke sensors have been proposed that can determine the type of smoke, including not only smoke from a fire but also smoke from cooking, steam in a bathroom and the like. For example, Patent Document 1 discloses a smoke sensor using a plurality of light emitting devices with different wavelengths. This smoke sensor includes: a light-emitting device that emits a light having a relatively short wavelength toward an environment in which smoke may exist (e.g., blue light-emitting diode (LED)); a light-emitting device that emits a light having a relatively long wavelength toward the environment (e.g., near-infrared light-emitting diode (LED)); and one light-receiving device provided at a location in which the lights emitted from these light-emitting devices are not directly received. Then, this smoke sensor causes the light-emitting devices to emit lights at timings different from each other, obtains the amounts of received lights from the light-receiving device that receives the lights scattered by smoke, and determines the type of the smoke based on the obtained amounts of received lights.

PRIOR ART DOCUMENT

Patent Document

[Patent Document 1] JP-A-11-023458

SUMMARY OF THE INVENTION

Problems to be Solved by the Invention

However, in the conventional smoke sensor as described above, since the two light-emitting devices emit lights at different timings and the emitted lights are received by the light-receiving device at different timings, the amounts of received lights output from the light-receiving device do not correspond to the same smoke, making it difficult to accurately determine the type of the smoke.

In view of the above, it is an object of the present invention to provide a smoke sensing system, a smoke sensor and a receiver that can accurately determine the type of smoke.

Means for Solving the Problems

In order to solve the problem described above and achieve the object, the smoke sensing system according to claim 1 and the smoke sensor according to claim 13 include: a light-projecting means for projecting detection light toward a monitored area; a plurality of light-receiving means for receiving the detection light scattered by particles existing in the monitored area, the plurality of light-receiving means being arranged such that the angles between the light-receiving axes of the plurality of light-receiving means and the light-projecting axis of the light-projecting means are different from one another; a smoke type determining means for determining the type of smoke generated in the monitored area based on the output values output from the plurality of light-receiving means; and a fire determining means for determining whether or not a fire has occurred in the monitored area, based on the output values output from the plurality of light-receiving means.

Furthermore, in accordance with the smoke sensing system according to claim 1, in the smoke sensing system according to claim 2, the smoke type determining means determines the type of smoke generated in the monitored area based on the ratios between the output values output from the plurality of light-receiving means.

Furthermore, in accordance with the smoke sensing system according to claim 1 or 2, in the smoke sensing system according to claim 3, the smoke type determining means determines whether or not the type of smoke generated in the monitored area is to be determined, based on the output value from a light-receiving means with the largest output value of the plurality of light-receiving means.

Furthermore, in accordance with the smoke sensing system according to any one of claims 1 to 3, in the smoke sensing system according to claim 4, the fire determining means determines whether or not a fire has occurred in the monitored area, based on the output value from a light-receiving means with the largest output value of the plurality of light-receiving means.

Furthermore, in accordance with the smoke sensing system according to claim 1 or 2, in the smoke sensing system according to claim 5, the smoke type determining means determines whether or not the type of smoke generated in the monitored area is to be determined, based on the output value from a light-receiving means having the light-receiving axis at the smallest angle with the light-projecting axis of the light-projecting means, of the plurality of light-receiving means.

Furthermore, in accordance with the smoke sensing system according to any one of claims 1, 2 and 5, in the smoke sensing system according to claim 6, the fire determining means determines whether or not a fire has occurred in the monitored area, based on the output value from a light-receiving means having the light-receiving axis at the smallest angle with the light-projecting axis of the light-projecting means, of the plurality of light-receiving means.

Furthermore, in accordance with the smoke sensing system according to any one of claims 1 to 6, in the smoke sensing system according to claim 7, the fire determining means changes the criterion for determining whether or not a fire has occurred in the monitored area, based on the type of the smoke determined by the smoke type determining means.

Furthermore, in accordance with the smoke sensing system according to any one of claims 1 to 6, in the smoke sensing system according to claim 8, the fire determining means corrects the output value output from the light-receiving means, based on the type of the smoke determined by the smoke type determining means.

Furthermore, in accordance with the smoke sensing system according to any one of claims 1 to 8, the smoke sensing system according to claim 9 includes an obstacle determining means for determining whether or not an obstacle exists in the monitored area, based on the output values output from the plurality of light-receiving means.

Furthermore, in accordance with the smoke sensing system according to claim 9, in the smoke sensing system according to claim 10, the obstacle determining means determines whether or not an obstacle exists in the monitored area, based on the total of the output values output from the plurality of light-receiving means.

Furthermore, in accordance with the smoke sensing system according to claim 9, in the smoke sensing system according to claim 11, the obstacle determining means determines whether or not an obstacle exists in the monitored area, based on the output value from a light-receiving means with the largest output value of the plurality of light-receiving means.

Furthermore, in accordance with the smoke sensing system according to claim 9, in the smoke sensing system according to claim 12, the obstacle determining means determines whether or not an obstacle exists in the monitored area, based on the output value from a light-receiving means having the light-receiving axis at the smallest angle with the light-projecting axis of the light-projecting means, of the plurality of light-receiving means.

Furthermore, the receiver according to claim 14 is a receiver for receiving an output value output from a smoke sensor comprising: a light-projecting means for projecting detection light toward a monitored area; and a plurality of light-receiving means for receiving the detection light scattered by particles existing in the monitored area, the receiver including: a smoke type determining means for determining the type of smoke generated in the monitored area based on the output value received from the smoke sensor; and a fire determining means for determining whether or not a fire has occurred in the monitored area, based on the output value received from the smoke sensor.

Advantage of the Invention

In accordance with the smoke sensing system according to claim 1, the smoke sensor according to claim 13 or the receiver according to claim 14, the smoke type determining means determines the type of smoke based on the output values output from a plurality of light-receiving means placed at different locations with respect to one light-projecting means, the output values being output in response to the detection light scattered in the monitored area. So, the plurality of light-receiving means receive the detection light from the light-projecting means at the same timing, which allows determining the type of smoke based on the output values output from the plurality of light-receiving means in response to the same smoke generated in the monitored area, thereby achieving accurate determination of the type of smoke.

Furthermore, in accordance with the smoke sensing system according to claim 2, the smoke type determining means determines the type of smoke based on the ratios between the output values output from the plurality of light-receiving means, which allows determining the type of smoke, not depending on the magnitude of the output values output from the plurality of light-receiving means, thereby achieving further accurate determination of the type of smoke.

Furthermore, in accordance with the smoke sensing system according to claim 3, the smoke type determining means determines whether or not the type of smoke is to be determined, based on the output value from a light-receiving means with the largest output value, which allows determining whether or not the type of smoke is to be determined, using a light-receiving means that can precisely detect smoke depending on the situation of smoke detection, thereby achieving accurate and quick determination of the type of smoke.

Furthermore, in accordance with the smoke sensing system according to claim 4, the fire determining means determines whether or not a fire has occurred, based on the output value from a light-receiving means with the largest output value, which allows determining whether or not a fire has occurred, using a light-receiving means that can precisely detect smoke depending on the situation of smoke detection, thereby achieving accurate and quick detection of a fire.

Furthermore, in accordance with the smoke sensing system according to claim 5, the smoke type determining means determines whether or not the type of smoke is to be determined, based on the output value from a light-receiving means having the light-receiving axis at the smallest angle with the light-projecting axis of the light-projecting means, which allows determining whether or not the type of smoke is to be determined, using a light-receiving means that can precisely detect smoke even when the detection light is not likely to be scattered by the smoke, thereby achieving accurate and quick determination of the type of smoke.

Furthermore, in accordance with the smoke sensing system according to claim 6, the fire determining means determines whether or not a fire has occurred, based on the output value of a light-receiving means having the light-receiving axis at the smallest angle with the light-projecting axis of the light-projecting means, which allows determining whether or not a fire has occurred, using a light-receiving means that can precisely detect smoke even when the detection light is not likely to be scattered by the smoke, thereby achieving accurate and quick detection of a fire.

Furthermore, in accordance with the smoke sensing system according to claim 7, the fire determining means changes the criterion for determining whether or not a fire has occurred in the monitored area, based on the type of the smoke determined by the smoke type determining means, which allows determining whether or not a fire has occurred, based on the criterion for the determination corresponding to the characteristic for each type of smoke, thereby achieving further accurate detection of a fire.

Furthermore, in accordance with the smoke sensing system according to claim 8, the fire determining means corrects the output value output from the light-receiving means, based on the type of the smoke determined by the smoke type determining means, which allows correcting the output value of the light-receiving means depending on the characteristic for each type of smoke, thereby achieving further accurate detection of a fire.

Furthermore, in accordance with the smoke sensing system according to claim 9, the obstacle determining means determines whether or not an obstacle exists, based on the output values output from the plurality of light-receiving means placed at different locations with respect to one light-projecting means, the output values being output in response to the detection light scattered in the monitored area, so the plurality of light-receiving means receive the detection light from the light-projecting means at the same timing, which allows determining whether or not an obstacle exists, based on the output values output from the plurality of light-receiving means in response to the same obstacle, thereby achieving accurate detection of an obstacle.

Furthermore, in accordance with the smoke sensing system according to claim 10, the obstacle determining means determines whether or not an obstacle exists, based on the total of the output values output from a plurality of light-receiving means placed at different locations, which allows determining whether or not an obstacle exists, by aggregating the output values output from the plurality of light-receiving means, thereby achieving further accurate detection of an obstacle.

Furthermore, in accordance with the smoke sensing system according to claim 11, the obstacle determining means determines whether or not an obstacle exists, based on the output value from a light-receiving means with the largest output value, which allows determining whether or not an obstacle exists, using a light-receiving means that can precisely detect an obstacle depending on the situation of obstacle detection, thereby achieving accurate and quick detection of an obstacle.

Furthermore, in accordance with the smoke sensing system according to claim 12, the obstacle determining means determines whether or not an obstacle exists in the monitored area, based on the output value from a light-receiving means having the light-receiving axis at the smallest angle with the light-projecting axis of the light-projecting means, which allows determining whether or not an obstacle exists, using a light-receiving means that can precisely detect an obstacle even when the detection light is not likely to be scattered by the obstacle, thereby achieving accurate and quick detection of obstacle.

MODE FOR CARRYING OUT THE INVENTION

Hereinafter, an embodiment of a smoke sensing system, a smoke sensor and a receiver in accordance with the invention is described in detail with reference to the accompanying drawings. First, a configuration of the embodiment is described. Then, a processing of the embodiment is described. Finally, a variation of the embodiment is described. However, the invention is not intended to be limited to the embodiment. Note that the embodiment is described in connection with a smoke sensor that is installed in a large-scale construction, such as a plant or building, or an underground mall or even in a room of an ordinary residence, such as a kitchen or bedroom, and is configured to sense smoke generated in a monitored area.

(Configuration of Smoke Sensor)

Figure 1:
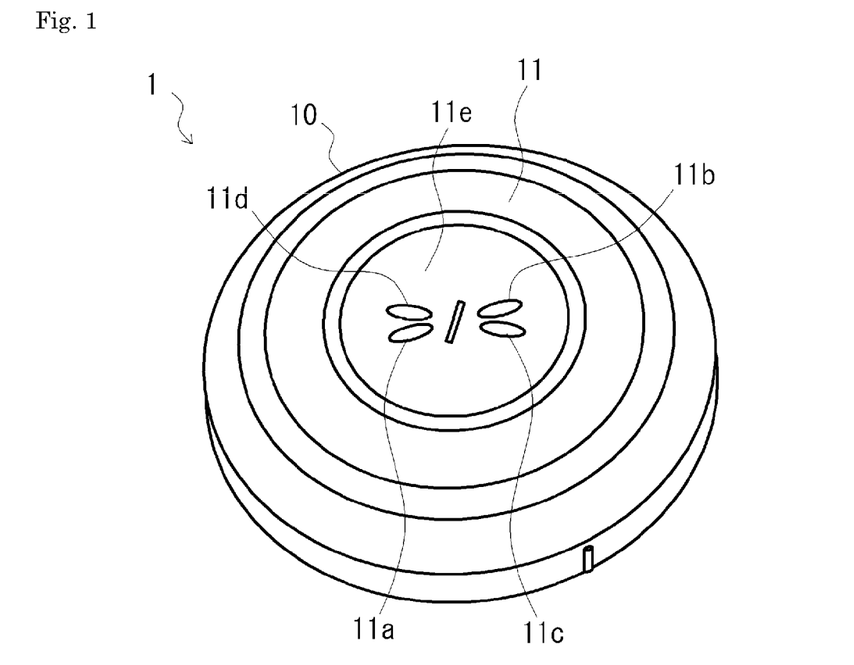
FIG. 1 is a perspective view of a smoke sensor in accordance with the embodiment.
Figure 2:
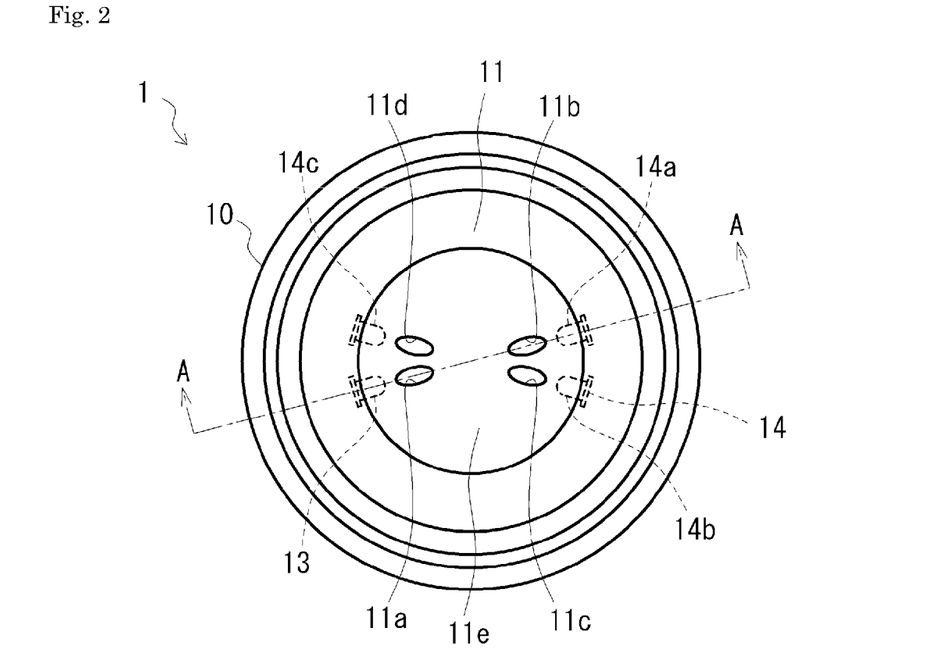
FIG. 2 is a plan view of FIG. 1.
Figure 3:
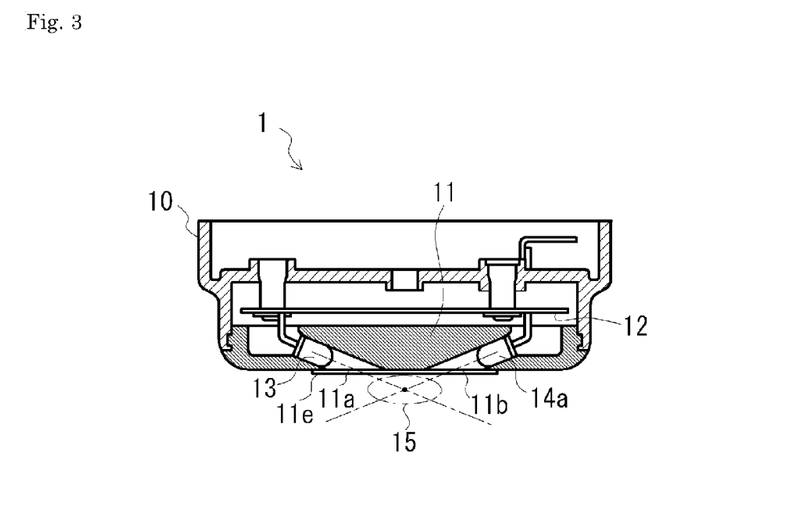
FIG. 3 is a cross-sectional view taken in the direction indicated by the arrows A-A in FIG. 2.

First, a configuration of a smoke sensor is described. FIG. 1 is a perspective view of the smoke sensor in accordance with the embodiment. FIG. 2 is a plan view of FIG. 1. FIG. 3 is a cross-sectional view taken in the direction indicated by the arrows A-A in FIG. 2.

As shown in FIG. 1, a smoke sensor 1 is placed in a monitored area in which generation of smoke is to be monitored. The smoke sensor 1 projects detection light toward the monitored area, receives the detection light scattered by particles existing in the monitored area, and monitors an output value output based on the received detection light. Also, as shown in FIGS. 2 and 3, the smoke sensor 1 includes a sensor body 10 that is a basic structure of the smoke sensor 1, and the bottom portion of the sensor body 10 is formed in a generally cylindrical shape with smooth curve. The sensor body 10 may be formed of any appropriate material, such as a resin. The sensor body 10 includes a holder 11, a circuit board 12, a light-projecting unit 13 and light-receiving units 14 (specifically, a first light-receiving unit 14a, a second light-receiving unit 14b and a third light-receiving unit 14c described later).

The holder 11 holds the light-projecting unit 13, the light-receiving units 14 and the circuit board 12. For example, the holder 11 holds in its bottom portion the light-projecting unit 13 and the light-receiving units 14, and holds above it the circuit board 12. The holder 11 is formed of an insulating material, such as a resin, and is placed in the bottom portion of the sensor body 10. The holder 11 may be connected to the sensor body 10 in any appropriate way. For example, the holder 11 may be connected to the sensor body 10 with a securing member, such as a screw. Furthermore, the bottom portion of the holder 11 is formed in a flat shape, in which openings 11a-11d are provided to hold the light-projecting unit 13 and the light-receiving units 14 exposed to the outside. Note that a thin-shaped, transparent cover 11e is provided on the bottom of the holder 11 to cover the openings 11a-11d in order to prevent dust and the like from getting into the smoke sensor 1 through the openings 11a-11d.

Figure 7:
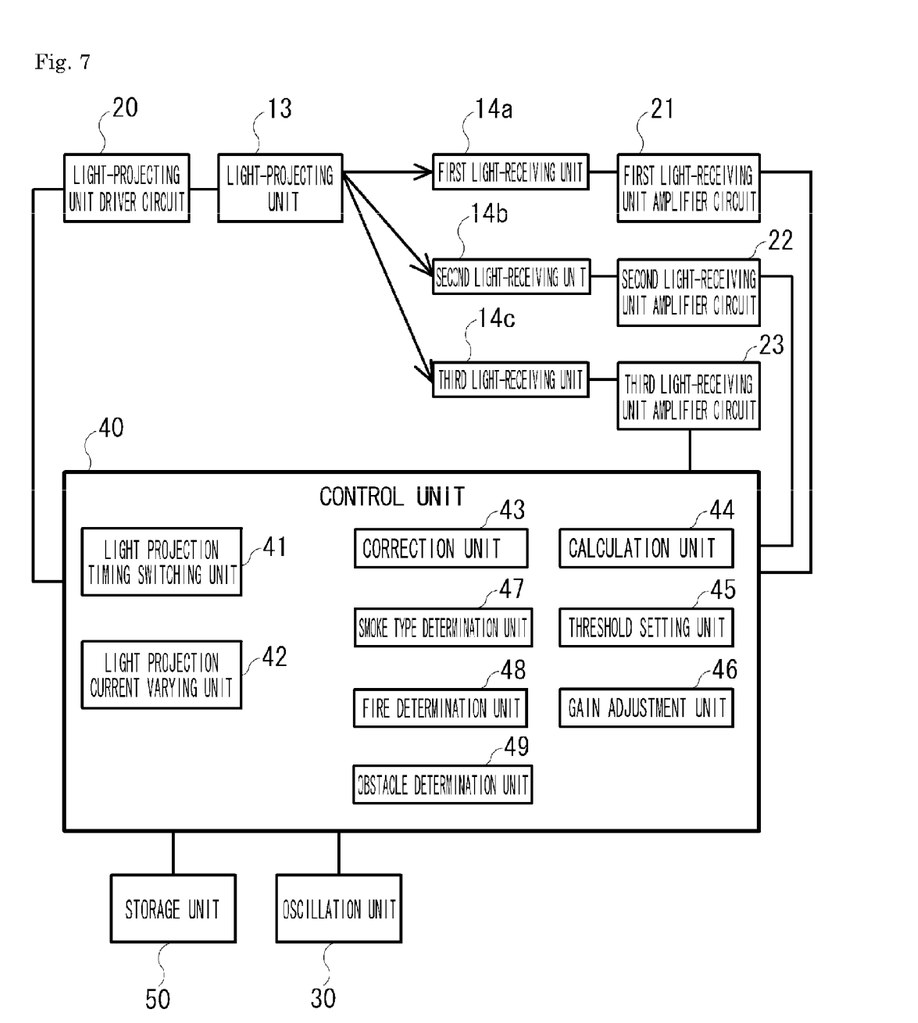
FIG. 7 is a block diagram conceptually showing the electrical configuration of the smoke sensor.

Various electric devices are mounted on the circuit board 12. As shown in FIG. 7 described later, the circuit board 12 includes a light-projecting unit driver circuit 20, a first light-receiving unit amplifier circuit 21, a second light-receiving unit amplifier circuit 22, a third light-receiving unit amplifier circuit 23, an oscillation unit 30, a control unit 40 and a storage unit 50 mounted thereon.

The light-projecting unit 13 is a light-projecting means for projecting toward the monitored area detection light to be used for detecting smoke. The light-projecting unit 13 may be configured in any appropriate way, and any appropriate wavelength may be used for projecting light from the light-projecting unit 13. For example, an infrared light-emitting diode (LED) may be used, which is a long-wavelength light-emitting device that emits light with a long wavelength of 870 nm.

The light-receiving units 14 is a light-receiving means for receiving detection light scattered by particles existing in the monitored area. Specifically, as shown in FIG. 2, in the embodiment, the light-receiving units 14 includes the first light-receiving unit 14a, the second light-receiving unit 14b and the third light-receiving unit 14c placed in the holder 11. The first light-receiving unit 14a, the second light-receiving unit 14b and the third light-receiving unit 14c may be configured in any appropriate way. For example, when the light-projecting unit 13 is a long-wavelength light-emitting device, such as an infrared LED, a long-wavelength light-receiving device having a photodiode that receives detection light from the long-wavelength light-emitting device, scattered by particles in the monitored area, may be used.

Thus, according to the configuration of the smoke sensor 1 shown in FIGS. 1 to 3, the light-projecting unit 13 projects detection light toward the outside of the smoke sensor 1 through the opening 11a and the transparent cover 11e, and the light-receiving units 14 receive the detection light through the transparent cover 11e and the openings 11b to 11d.

Accordingly, a detection space 15 for detecting smoke exists in the outside of the smoke sensor 1. This eliminates the need for providing the detection space 15 within the smoke sensor 1 as in the prior art, which can decrease the overall height of the smoke sensor 1, making the smoke sensor 1 thinner.

Figure 4:
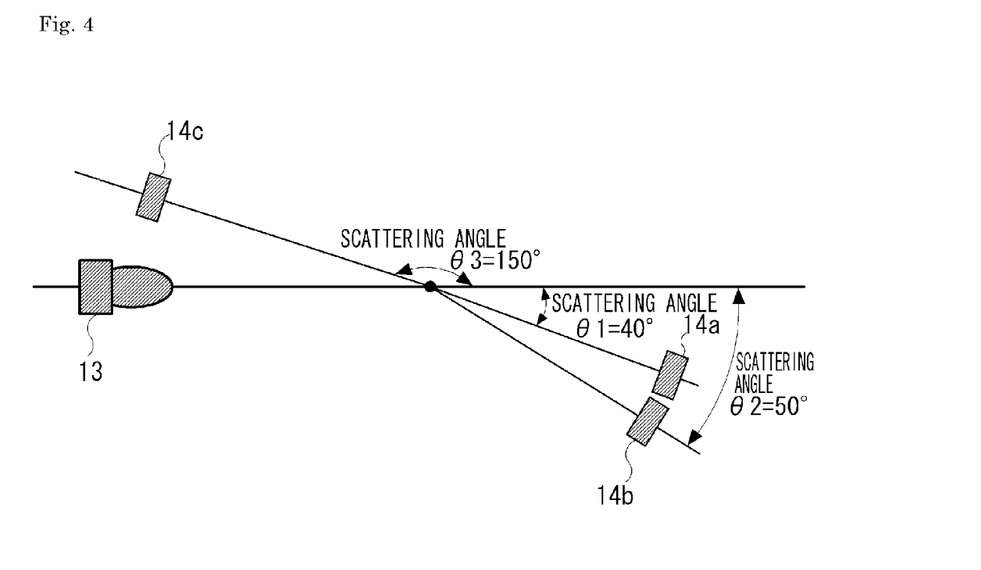
FIG. 4 is a view schematically illustrating the relation between a light-projecting unit and light-receiving units.

FIG. 4 schematically illustrates the relation between the light-projecting unit 13 and the light-receiving units 14. As shown in FIG. 4, the first light-receiving unit 14a, the second light-receiving unit 14b and the third light-receiving unit 14c are arranged such that the angle between the light-projecting axis of the light-projecting unit 13 and the light-receiving axis of the first light-receiving unit 14a (hereinafter referred to as a first scattering angle $\theta 1$), the angle between the light-projecting axis of the light-projecting unit 13 and the light-receiving axis of the second light-receiving unit 14b (hereinafter referred to as a second scattering angle $\theta 2$) and the angle between the light-projecting axis of the light-projecting unit 13 and the light-receiving axis of the third light-receiving unit 14c (hereinafter referred to as a third scattering angle $\theta 3$) are different from one another.

Figure 5:
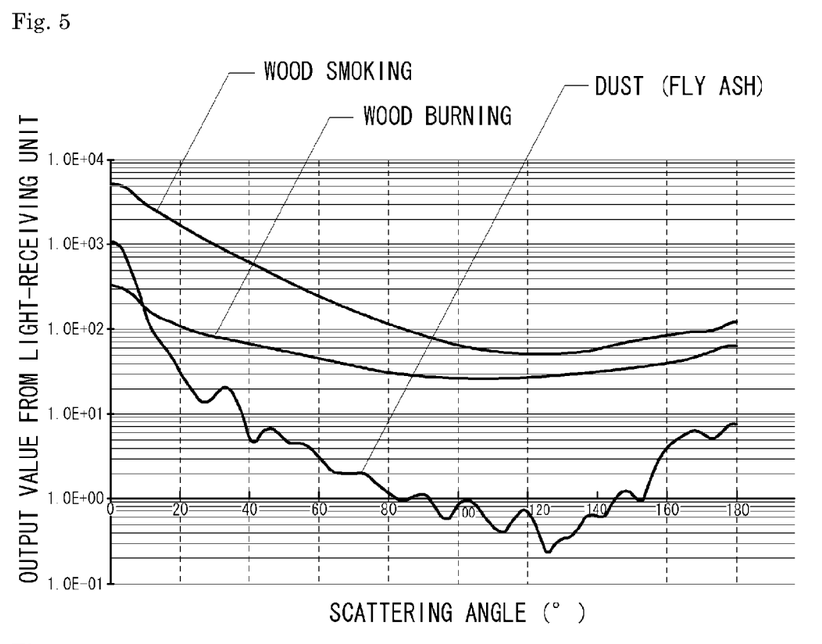
FIG. 5 is a view showing a result of analysis of the output value of the light-receiving units versus scattering angle.

Now, the setting of the first scattering angle $\theta 1$, the second scattering angle $\theta 2$ and the third scattering angle $\theta 3$ is described. FIG. 5 shows a result of analysis of the output value of the light-receiving units 14 versus the scattering angle, in which the vertical axis shows the output value of the light-receiving units 14, and the horizontal axis shows the scattering angle. As shown in FIG. 5, the output values for various smokes (due to wood burning, wood smoking and dust (fly ash in this example) in the case of FIG. 5) decrease as the scattering angle increases. Furthermore, in the range of scattering angle from 30° to 60°, the output values for the various smokes tend to vary largely; and, in the range of scattering angle from 140° to 160°, the difference between the output values for wood burning and wood smoking tends to be stable. On the other hand, in the range of scattering angle from 0° to 30°, since the light-receiving units 14 easily receive light directly from the light-projecting unit 13, the smoke sensor 1 finds difficulty in working as a smoke sensor; in the range of scattering angle from 60° to 140°, the output values for the various smokes vary small; and in the range of scattering angle from 160° to 180°, since the light-receiving units 14 are too close to the light-projecting unit 13, the smoke sensor 1 finds difficulty in working as a smoke sensor. As may be seen from the above, the optimum range of scattering angle for determining the type of smoke is from 30° to 60° and from 140° to 160°. Particularly for detecting smoke using a plurality of light-receiving units 14 as in the embodiment, arranging many of the light-receiving units 14 in the range of scattering angle from 30° to 60° in which the output values for the various smokes vary largely would facilitate determining the type of smoke.

Based on the above discussion, the first scattering angle $\theta 1$ and the second scattering angle $\theta 2$ are preferably set to within the range from 30° to 60°, and the third scattering angle $\theta 3$ is preferably set to within the range from 140° to 160°. So, in the embodiment, the first scattering angle $\theta 1$ is set to 40°, the second scattering angle $\theta 2$ is set to 50°, and the third scattering angle $\theta 3$ is set to 150°.

Figure 6:
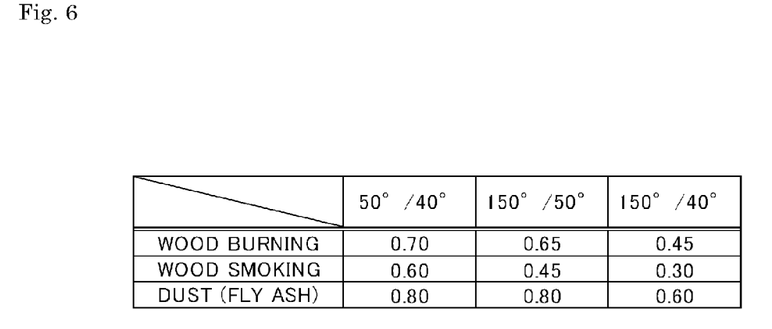
FIG. 6 is a view showing the ratios between the output values of the light-receiving units obtained through a verification experiment.

Next, a result of having verified whether or not the type of smoke can be actually determined, based on the first scattering angle $\theta 1$ of 40°, the second scattering angle $\theta 2$ of 50° and the third scattering angle $\theta 3$ of 150° set in the embodiment is described. FIG. 6 shows the ratios between the output values of the light-receiving units 14 obtained through the verification experiment. FIG. 6 shows, for each of the various smokes, the ratio between the output values of the scattering angles of 50° and 40° (hereinafter referred to as the output ratio)50°/40°; the ratio between the output values of the scattering angles of 150° and 50° (hereinafter referred to as the output ratio)150°/50°; and the ratio between the output values of the scattering angles of 150° and 40° (hereinafter referred to as the output ratio)150°/40°. As shown in FIG. 6, for wood burning, the output ratio 50°/40° is 0.70, the output ratio 150°/50° is 0.65 and the output ratio 150°/40° is 0.45; for wood smoking, the output ratio 50°/40° is 0.60, the output ratio 150°/50° is 0.45 and the output ratio 150°/40° is 0.30; and for dust, the output ratio 50°/40° is 0.80, the output ratio 150°/50° is 0.80 and the output ratio 150°/40° is 0.60.

As seen from the above, the output ratio varies depending on the type of smoke. This is because the scattering pattern varies depending on the particle size, particle shape and refraction index of smoke. For example, for wood burning, probably, since the particle size is small, backward scattering have relatively often occurred in addition to forward scattering according to Mie's theorem. For wood smoking, probably, forward scattering probably have often occurred, but backward scattering have not often occurred. For dust, because of various particle sizes, backward scattering due to multiple scattering may also have often occurred. Furthermore, since the differences between the output ratios of wood burning and wood smoking are as follows: for the output ratio 50°/40°, 0.70-0.60=0.10; for the output ratio 150°/50°, 0.65-0.45=0.20; and for the output ratio 150°/40°, 0.45-0.30=0.15, the output ratio for wood smoking may be smaller than that for wood burning. Thus, since the output ratios for the plurality of scattering angles are different from one another depending on the type of smoke, it is verified that the type of smoke can be determined based on the first scattering angle $\theta 1$ of 40°, the second scattering angle $\theta 2$ of 50° and the third scattering angle $\theta 3$ of 150° set in the embodiment.

(Electrical Configuration of Smoke Sensor)

Next, the electrical configuration of the smoke sensor 1 is described. FIG. 7 is a block diagram conceptually showing the electrical configuration of the smoke sensor 1. The smoke sensor 1 includes a light-projecting unit driver circuit 20, a first light-receiving unit amplifier circuit 21, a second light-receiving unit amplifier circuit 22, a third light-receiving unit amplifier circuit 23, an oscillation unit 30, a control unit 40 and a storage unit 50.

The light-projecting unit driver circuit 20 is a light-projecting unit driving means for supplying power to the light-projecting unit 13 to drive it to project light.

The first light-receiving unit amplifier circuit 21 is a first light-receiving unit amplifying means for amplifying and outputting to the control unit 40 the output value output from the first light-receiving unit 14a that receives detection light from the light-projecting unit 13 scattered in a monitored area.

The second light-receiving unit amplifier circuit 22 is a second light-receiving unit amplifying means for amplifying and outputting to the control unit 40 the output value output from the second light-receiving unit 14b that receives detection light from the light-projecting unit 13 scattered in a monitored area.

The third light-receiving unit amplifier circuit 23 is a third light-receiving unit amplifying means for amplifying and outputting to the control unit 40 the output value output from the third light-receiving unit 14c that receives detection light from the light-projecting unit 13 scattered in a monitored area.

The oscillation unit 30 is an oscillating means for outputting reference signal for causing the light-projecting unit 13 to project detection light at a predetermined timing.

The control unit 40 is a controlling means for performing various control of the smoke sensor 1. The control unit 40 may be configured in any appropriate way. For example, the control unit 40 may be configured as a central processing unit (CPU) that calls, analyzes and executes a program stored in the storage unit 50. In the embodiment, the control unit 40 includes a light projection timing switching unit 41, a light projection current varying unit 42, a correction unit 43, a calculation unit 44, a threshold setting unit 45, a gain adjustment unit 46, a smoke type determination unit 47, a fire determination unit 48 and an obstacle determination unit 49. The light projection timing switching unit 41 is a light projection timing switching means for gradually switching the timing of projecting light of the light-projecting unit 13 based on the reference signal output from the oscillation unit 30. The light projection current varying unit 42 is a light projection current varying means for adjusting the intensity of the light-projecting unit 13. The correction unit 43 is a correcting means for correcting the output values output from the first light-receiving unit 14a, the second light-receiving unit 14b and the third light-receiving unit 14c. The calculation unit 44 is a calculating means for performing a predetermined calculation using the output values output from the first light-receiving unit 14a, the second light-receiving unit 14b and the third light-receiving unit 14c. The threshold setting unit 45 is a threshold setting means for setting a threshold for determining by the fire determination unit 48 whether or not a fire has occurred. The gain adjustment unit 46 is a gain adjusting means for adjusting the gains of the first light-receiving unit amplifier circuit 21, the second light-receiving unit amplifier circuit 22 and the third light-receiving unit amplifier circuit 23 in order to improve the output sensitivity of the first light-receiving unit 14a, the second light-receiving unit 14b and the third light-receiving unit 14c. The smoke type determination unit 47 is a smoke type determining means for determining the type of smoke generated in the monitored area based on the output values output from the first light-receiving unit 14a, the second light-receiving unit 14b and the third light-receiving unit 14c. The fire determination unit 48 is a fire determining means for determining whether or not a fire has occurred in the monitored area, based on the output values output from the first light-receiving unit 14a, the second light-receiving unit 14b and the third light-receiving unit 14c. The obstacle determination unit 49 is an obstacle determining means for determining whether or not an obstacle exists in the monitored area, based on the output values output from the first light-receiving unit 14a, the second light-receiving unit 14b and the third light-receiving unit 14c.

The storage unit 50 is a storage means for storing programs and various data (e.g., a threshold for determining whether or not a fire has occurred, or the like) necessary for controlling by the control unit 40. The storage unit 50 may be configured in any appropriate way. For example, a nonvolatile storage medium, such as a flash memory or erasable programmable read only memory (EPROM), may be used for the storage unit 50.

(Processing)

The processing performed by the smoke sensor 1 configured as above is described below. This processing is broadly divided into a fire detection processing and an obstacle processing. The processings described below are on the assumption that the smoke sensor 1 is always powered on and ready to perform the processings according to a program stored in the storage unit 50. Also the processings are to be performed by the control unit 40 unless otherwise stated.

(Processing-Fire Detection Processing)

Figure 8:
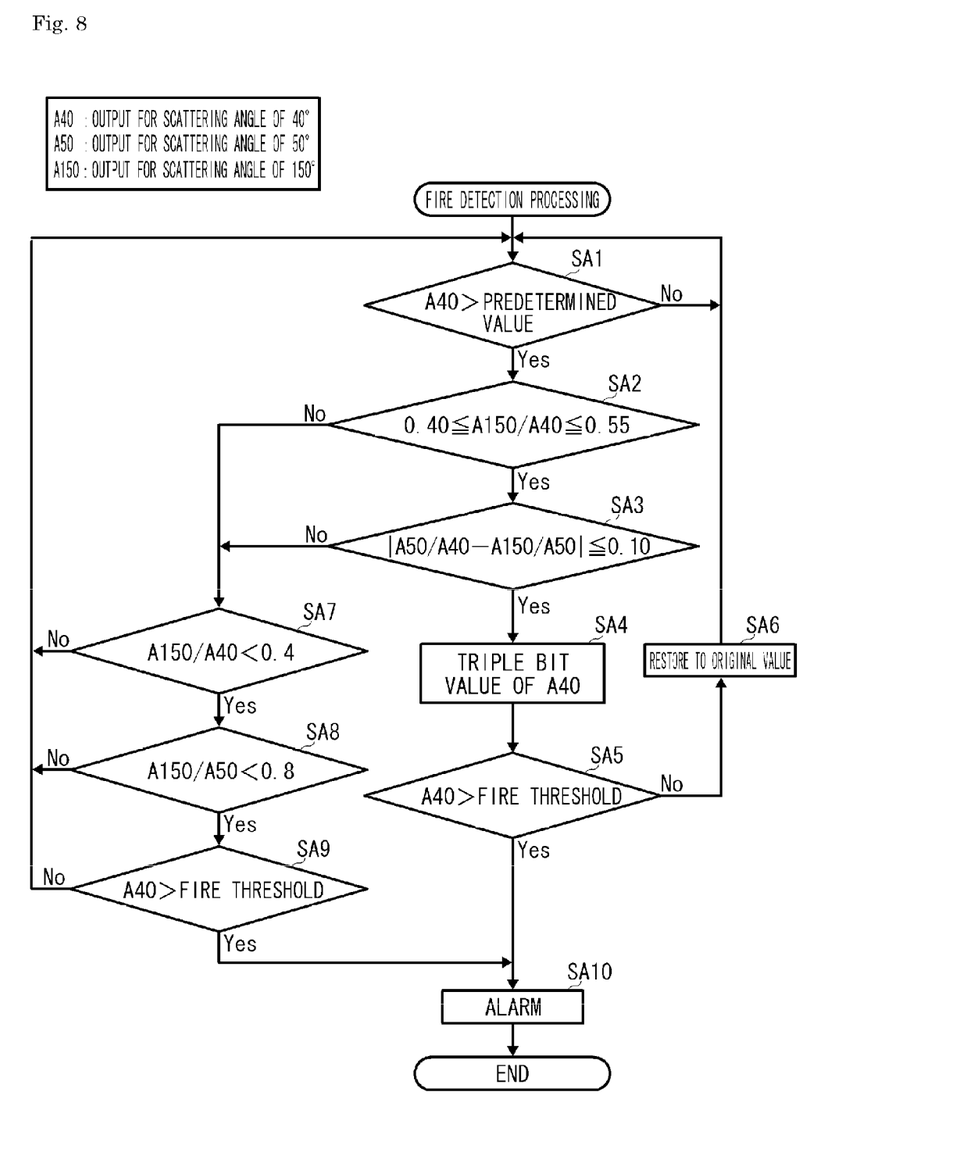
FIG. 8 is a flowchart of a fire detection processing.

First, the fire detection processing is described. The fire detection processing is a processing of detecting a fire occurring in the monitored area. This processing is broadly divided into a smoke type determination processing and a fire occurrence determination processing. The smoke type determination processing is a processing of determining the type of smoke generated in the monitored area. The fire occurrence determination processing is a processing of determining whether or not a fire has occurred in the monitored area. In the fire detection processing, the smoke type determination processing is performed (mainly by the smoke type determination unit 47) before the fire occurrence determination processing is performed (mainly by the fire determination unit 48). FIG. 8 is a flowchart of the fire detection processing. In the following description, "step" is abbreviated to "S."

First, in order to determine whether or not smoke has been generated which may be an indication of a fire in the monitored area, the smoke type determination unit 47 monitors the output value output from the first light-receiving unit 14a with the smallest scattering angle (hereinafter referred to as the output value A40 of the first light-receiving unit 14a), of the first light-receiving unit 14a, the second light-receiving unit 14b and the third light-receiving unit 14c (SA1). At this time, the first light-receiving unit 14a receives detection light that is projected in synchronization with the reference signal output from the oscillation unit 30 toward the monitored area from the light-projecting unit 13 supplied with power by the light-projecting unit driver circuit 20, the detection light being scattered by particles in the monitored area, and outputs the output value A40 through the first light-receiving unit amplifier circuit 21. Thus, the output value A40 of the first light-receiving unit 14a is output from the first light-receiving unit 14a through the first light-receiving unit amplifier circuit 21. Similarly to this, the output value output from the second light-receiving unit 14b (hereinafter referred to as the output value A50 of the second light-receiving unit 14b) is output from the second light-receiving unit 14b through the second light-receiving unit amplifier circuit 22, and the output value output from the third light-receiving unit 14c (hereinafter referred to as the output value A150 of the third light-receiving unit 14c) is output from the third light-receiving unit 14c through the third light-receiving unit amplifier circuit 23. Note that the timing of projection of the detection light projected by the light-projecting unit 13 can be changed as desired, by switching the timing based on the reference signal output from the oscillation unit 30 using the light projection timing switching unit 41.

The reason smoke is monitored in the processing of SA1 based on the first light-receiving unit 14a with the smallest scattering angle is that, as shown in FIG. 5, for smoke generated by a fire, the smaller the scattering angle is, the larger the output value output from the light-receiving unit 14 is. This means that the smaller the scattering angle is, the higher the accuracy of smoke detection of the light-receiving unit 14 is. Accordingly, in the embodiment, since the magnitude relation between the output values for the first to third scattering angles is the first scattering angle θ1 (=40°)>the second scattering angle θ2 (=50°)>the third scattering angle θ3 (=150°), the processing of SA1 is performed based on the first light-receiving unit 14a with the first scattering angle θ1.

However, the light-receiving unit 14 to be used in the processing of SA1 is not limited to the first light-receiving unit 14a with the smallest scattering angle. For example, the smoke type determination unit 47 may determine whether or not smoke has been generated which may be an indication of a fire in the monitored area, by comparing as necessary the output values of the first light-receiving unit 14a, the second light-receiving unit 14*b* and the third light-receiving unit 14*c* to determine the light-receiving unit 14 with the largest output value, then obtaining the output value output from the determined light-receiving unit 14, and then mutually comparing the obtained output value and a predetermined value stored in the storage unit 50. This allows the smoke sensor 1 to determine the type of smoke using the light-receiving unit 14 with the high accuracy of smoke detection depending on the situation of smoke detection. Note that the light-receiving unit 14 to be used in the processings of SA5, SA9, SB5 and SB9 described later may be determined using the above determination method. In the embodiment, the first light-receiving unit 14*a* is used also in the processings of SA5, SA9, SB5 and SB9 described later.

If the output value A40 of the first light-receiving unit has exceeded a predetermined value (SA1, Yes), it is determined that smoke has been generated which may be an indication of a fire in the monitored area. Then, the smoke type determination unit 47 performs processing of determining the type of smoke being generated. For example, the smoke type determination unit 47 performs processing of determining whether or not the type of the smoke having been generated in the monitored area is the type of smoke that is generated when a flaming fire occurs (for example, when a wood burning fire occurs) based on the output values output from the first light-receiving unit 14*a*, the second light-receiving unit 14*b* and the third light-receiving unit 14*c*. In the embodiment, two-stage determination is performed as follows. The first determination is performed based on the output ratio of the output value A150 of the third light-receiving unit 14*c* and the output value A40 of the first light-receiving unit 14*a* (hereinafter referred to as the output ratio A150/A40). The next determination is performed based on the difference between the output ratio of the output value A50 of the second light-receiving unit 14*b* and the output value A40 of the first light-receiving unit 14*a* (hereinafter referred to as the output ratio A50/A40) and the output ratio of the output value A150 of the third light-receiving unit 14*c* and the output value A50 of the second light-receiving unit 14*b* (hereinafter referred to as the output ratio A150/A50).

Specifically, in the first determination, the calculation unit 44 calculates the output ratio A150/A40, then the smoke type determination unit 47 determines whether or not the output ratio A150/A40 calculated by the calculation unit 44 satisfies $0.40 \leq A150/A40 \leq 0.55$ (SA2). The reason the determination thresholds of SA2 are set to 0.40 and 0.55 is that it is intended to exclude any type of smoke other than the type of smoke due to wood burning by causing the output ratio for wood burning (=0.45) to satisfy a requirement and causing the output ratio for wood smoking (=0.30) and the output ratio for dust (=0.60) not to satisfy the requirement, based on the output ratios 150°/40° for the various types of smokes shown in FIG. 6. Then, if the output ratio A150/A40 satisfies 0.40 A150/A40 0.55 (SA2, Yes), the processing proceeds to the next determination.

Then, in the next determination, the calculation unit 44 calculates the output ratios A50/A40 and A150/A50, then the calculation unit 44 calculates the absolute value of the difference between the output ratios A50/A40 and A150/A50, and then the smoke type determination unit 47 determines whether or not the absolute value of the difference between the output ratios A50/A40 and A150/A50 satisfies $|A50/A40 - A150/A50| \leq 0.10$ (SA3). The reason the determination threshold of SA3 is set to 0.10 is that it is intended to exclude any type of smoke other than the type of smoke due to wood burning by causing the absolute value of the difference for wood burning (=0.05) to satisfy a requirement and causing the absolute value of the difference for wood smoking (=0.15) not to satisfy the requirement, based on the absolute value of the difference between the output ratios of 50°/40° and 150°/50° shown in FIG. 6.

Then, if the absolute value of the difference between the output ratios A50/A40 and A150/A50 satisfies $|A50/A40 - A150/A50| \leq 0.10$ (SA3, Yes), it is determined that the smoke having been generated in the monitored area is due to a flaming fire. Furthermore, in order to determine whether or not a fire has actually occurred in the monitored area, the fire determination unit 48 monitors the output value A40 of the first light-receiving unit 14*a*. In the embodiment, the correction unit 43 triples the bit value of the output value A40 of the first light-receiving unit 14*a* (SA4), then the fire determination unit 48 determines whether or not the output value A40 of the first light-receiving unit 14*a* amplified by the correction unit 43 exceeds a threshold set by the threshold setting unit 45 (SA5). The reason, in the processing of SA4, the output value A40 of the first light-receiving unit 14*a* is corrected is that, since the amount of smoke generated by a flaming fire is smaller than the amount of smoke generated by a smoking fire, the output value A40 of the first light-receiving unit 14*a* is small, so, when the threshold for determining a flaming fire in SA5 is the same as the threshold for determining a smoking fire in SA9 described later, the output value A40 of the first light-receiving unit 14*a* may not exceed the threshold when a flaming fire occurs.

Then, if the output value A40 of the first light-receiving unit 14*a* amplified by the correction unit 43 falls below the threshold set by the threshold setting unit 45 (SA5, No), it is determined that a flaming fire has not occurred in the monitored area. Then, the correction unit 43 restores the bit value of the output value A40 of the first light-receiving unit 14*a* amplified in SA4 to the original value (SA6), then the fire determination unit 48 returns the processing to the beginning of SA1. On the other hand, if the output value A40 of the first light-receiving unit 14*a* amplified by the correction unit 43 exceeds the threshold set by the threshold setting unit 45 (SA5, Yes), it is determined that a flaming fire has occurred in the monitored area. Then, the fire determination unit 48 outputs an alarm signal to a receiver or the like (not shown) placed in the monitored area or the other area (SA10). This is the end of the fire detection processing. Note that, in the processing of SA10, when outputting the alarm signal to the receiver or the like not shown, the control unit 40 may output a signal identifying the type of smoke along with the alarm signal. Also, when the smoke sensor 1 sounds an alarm on the occurrence of a fire, the control unit 40 may control to change the type of the alarm sound depending on the type of smoke.

On the other hand, if the output ratio A150/A40 does not satisfy $0.40 \leq A150/A40 \leq 0.55$ (SA2, No), or if the absolute value of the difference between the output ratios A50/A40 and A150/A50 does not satisfy $|A50/A40 - A150/A50| \leq 0.10$ (SA3, No), it is determined that smoke other than smoke generated by a flaming fire has been generated in the monitored area. Then, the smoke type determination unit 47 performs processing of determining whether or not the type of the smoke having been generated in the monitored area is the type of smoke generated by a smoking fire (e.g., a fire due to wood smoking). In the embodiment, two-stage determination is performed as follows. In the first determination, the type of smoke generated by a smoking fire is determined based on the output ratio A150/A40. In the next determination, the type of smoke generated by a smoking fire is determined based on the output ratio A150/A50.

Specifically, in the first determination, the smoke type determination unit 47 determines whether or not the output ratio A150/A40 satisfies A150/A40<0.40 (SA7). The reason the determination thresholds of SA7 is set to 0.40 is that it is intended to exclude any type of smoke other than the type of smoke due to wood smoking by causing the output ratio for wood smoking (=0.30) to satisfy a requirement and causing the output ratio for wood burning (=0.45) and the output ratio for dust (=0.60) not to satisfy the requirement, based on the output ratios 150°/40° shown in FIG. 6. Then, if the output ratio A150/A40 satisfies A150/A40<0.40 (SA7, Yes), the processing proceeds to the next determination.

Then, in the next determination, the smoke type determination unit 47 determines whether or not the output ratio A150/A50 satisfies A150/A50<0.80 (SA8). The reason the determination thresholds of SA8 is set to 0.80 is that it is intended to exclude any type of smoke other than the type of smoke due to wood smoking by causing the output ratio for wood smoking (=0.45) to satisfy a requirement and causing the output ratio for dust (=0.80) not to satisfy the requirement, based on the output ratios 150°/50° shown in FIG. 6.

Then, if the output ratio A150/A40 does not satisfy A150/A40<0.40 (SA7, No) or if the output ratio A150/A50 does not satisfy A150/A50<0.80 (SA8, No), it is determined that smoke not relating to a fire (e.g., smoke from cooking, steam in a bathroom or the like) has been generated in the monitored area, then the smoke type determination unit 47 returns the processing to the beginning of SA1.

On the other hand, if the output ratio A150/A50 satisfies A150/A50<0.80 (SA8, Yes), it is determined that the smoke having been generated in the monitored area is due to a smoking fire. Furthermore, in order to determine whether or not a fire has actually occurred in the monitored area, the fire determination unit 48 monitors the output value A40 of the first light-receiving unit 14*a*. In the embodiment, the fire determination unit 48 determines whether or not the output value A40 of the first light-receiving unit 14*a* exceeds a threshold set by the threshold setting unit 45 (SA9). Then, if the output value A40 of the first light-receiving unit 14*a* falls below the threshold set by the threshold setting unit 45 (SA9, No), it is determined that a smoking fire has not occurred in the monitored area. Then, the fire determination unit 48 returns the processing to the beginning of SA1. On the other hand, if the output value A40 of the first light-receiving unit 14*a* exceeds the threshold set by the threshold setting unit 45 (SA9, Yes), it is determined that a smoking fire has occurred in the monitored area. Then, the fire determination unit 48 outputs an alarm signal to a receiver or the like (not shown) placed in the monitored area or the other area (SA10). This is the end of the fire detection processing. The reason, in the processing of SA9, the output value A40 of the first light-receiving unit 14*a* amplified by the correction unit 43 is not used, unlike the processing of SA5, is that, since the amount of smoke generated by a smoking fire is larger than the amount of smoke generated by a flaming fire, the output value A40 of the first light-receiving unit 14*a* is large, so, when the threshold for determining a smoking fire in SA9 is the same as the threshold for determining a flaming fire in SA5, the output value A40 of the first light-receiving unit 14*a* exceeds the threshold when a smoking fire occurs, even without correcting the threshold.

(Processing-Obstacle Processing)

Figure 9:
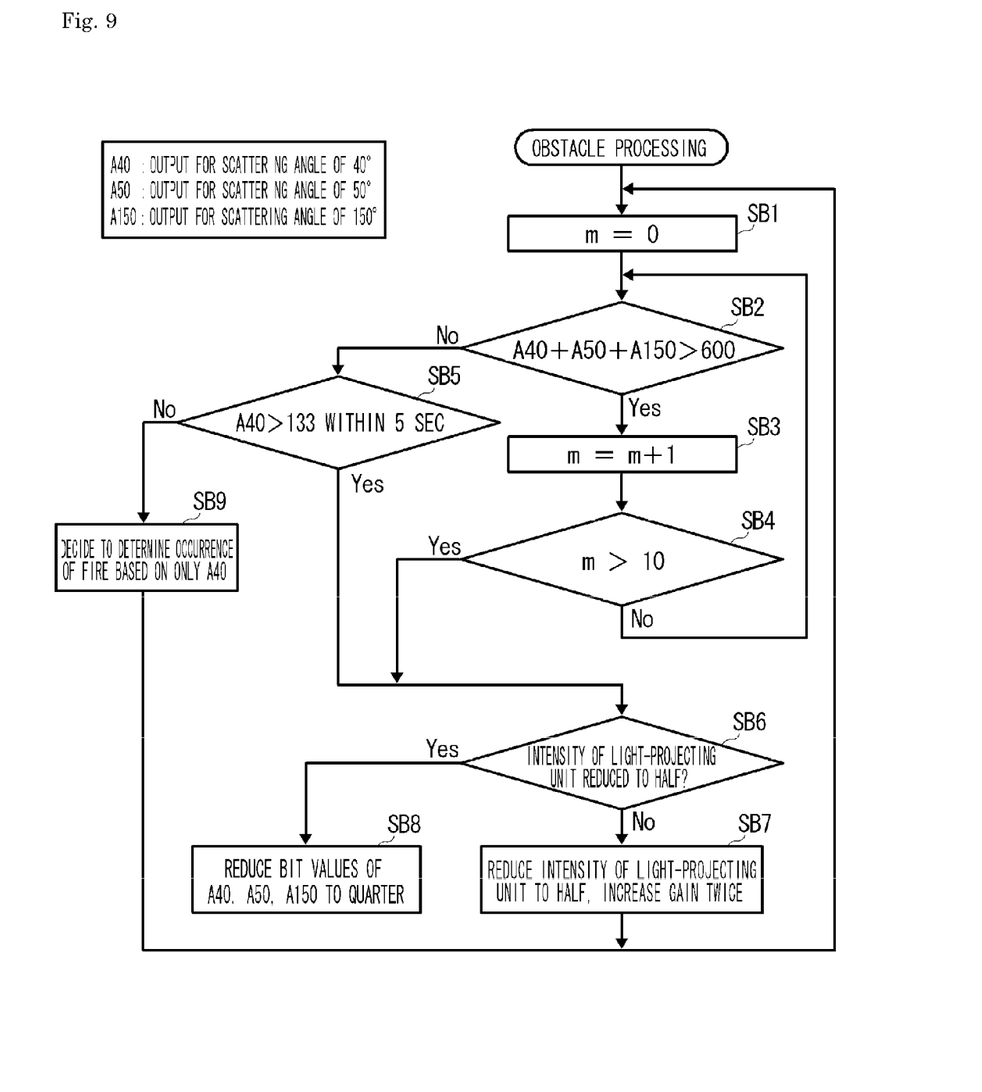
FIG. 9 is a flowchart of an obstacle processing.

Next, the obstacle processing is described. This processing is a processing of determining whether or not an obstacle exists in the monitored area. FIG. 9 is a flowchart of the obstacle processing.

First, in order to determine whether or not an obstacle exists in the monitored area, the obstacle determination unit 49 monitors the output value A40 of the first light-receiving unit 14*a*, the output value A50 of the second light-receiving unit 14*b* and the output value A150 of the third light-receiving unit 14*c*. In the embodiment, since the output values output from the first light-receiving unit 14*a*, the second light-receiving unit 14*b* and the third light-receiving unit 14*c* may be intensified by noise or the like to cause false detection of an obstacle, the processing of determining whether or not an obstacle exists is repeated in order to avoid the false detection of an obstacle. First, in order to initialize a variable to be used in the following processings, the repeat count of processing m is initialized to 0 (SB1). Next, the calculation unit 44 calculates the total of the output value A40 of the first light-receiving unit 14*a*, the output value A50 of the second light-receiving unit 14*b* and the output value A150 of the third light-receiving unit 14*c*, then the obstacle determination unit 49 determines whether or not the total calculated by the calculation unit 44 satisfies A40+A50+A150>600 (SB2). The reason the determination threshold for SB2 is set to 600 is that, in the processing in which it is determined that an obstacle exists when the total of the output value A40 of the first light-receiving unit 14*a*, the output value A50 of the second light-receiving unit 14*b* and the output value A150 of the third light-receiving unit 14*c* becomes close to the maximum output, since, assuming that the maximum output of one of the light-receiving units 14 is 255 bits, the total of the maximum outputs of the three light-receiving units 14 is 765 bits, it is intended to determine whether or not an obstacle exists, using a value close to the total (600 bits in this case).

Then, if the total of the output value A40 of the first light-receiving unit 14*a*, the output value A50 of the second light-receiving unit 14*b* and the output value A150 of the third light-receiving unit 14*c* satisfies A40+A50+A150>600 (SA2, Yes), it is determined that an obstacle may exist in the monitored area. Then, the obstacle determination unit 49 updates the repeat count m by incrementing the repeat count m by one (SB3). In the embodiment, the obstacle determination unit 49 updates the repeat count m to 0+1=1 (SB3). Then, the obstacle determination unit 49 monitors the repeat count m updated in SB3 (SB4) and repeats the processing of SB2 and SB3 until the repeat count m exceeds 10.

On the other hand, if the total of the output value A40 of the first light-receiving unit 14*a*, the output value A50 of the second light-receiving unit 14*b* and the output value A150 of the third light-receiving unit 14*c* does not satisfy A40+A50+A150>600 (SB2, No), in order to further determine whether or not an obstacle exists in the monitored area, based on the output value of the first light-receiving unit 14*a* having the light-receiving axis at the smallest angle with the light-projecting axis of the light-projecting unit 13, of the first light-receiving unit 14*a*, the second light-receiving unit 14*b* and the third light-receiving unit 14*c*, the obstacle determination unit 49 monitors the output value A40 of the first light-receiving unit 14*a*. In the embodiment, the obstacle determination unit 49 determines whether or not the output value A40 of the first light-receiving unit 14*a* satisfies A40>133 within a predetermined time after the first light-receiving unit 14*a* receives detection light (within 5 seconds in this case) (SB5). The reason the output value A40 of the first light-receiving unit 14*a* within a predetermined time is used to perform the processing of SB5 is that, since an obstacle is more likely to scatter detection light than smoke, it is intended to separate the output value for an obstacle from the output value for smoke based on the fact that the rate of rise per unit time in the output value for an obstacle is higher than that for smoke. Furthermore, the reason the determination threshold for SB5 is set to 133 is that it is intended to determine whether or not the smoke sensor 1 can detect smoke with the maximum smoke sensitivity without being saturated even when the output value A40 of the first light-receiving unit 14a is intensified by noise or the like. Specifically, the bit value of the output value A40 when the smoke sensor 1 is saturated is 255 bits, the maximum smoke sensitivity of a common smoke sensor 1 is 17%/m, and, in this case, for every 1%/m increase in smoke density, the output value A40 increases by 7.2 bits, so the determination threshold for SB5 is given by extracting an increase in bits when a smoke density of 17%/m is detected from a bit value when the smoke sensor 1 is saturated, that is 255 bits−122 (≈17×7.2) bits=133 bits.

Then, if the repeat count m updated in SB3 exceeds 10 (SB4, Yes), or if the output value A40 of the first light-receiving unit 14a satisfies A40>133 within 5 seconds after the first light-receiving unit 14a receives detection light (SB5, Yes), it is determined that an obstacle may exist in the monitored area. Then, in order to further determine that the obstacle surely exists, the obstacle determination unit 49 reduces the intensity of the light-projecting unit 13 below the normal level to perform again the processing of determining whether or not an obstacle exists in the monitored area. In the embodiment, since the intensity of the light-projecting unit 13 is at the normal level (SB6, No), the light projection current varying unit 42 reduces the intensity of the light-projecting unit 13 to half the normal level, and the gain adjustment unit 46 increases the gains of the first light-receiving unit 14a, the second light-receiving unit 14b and the third light-receiving unit 14c to twice the normal level (SB7). However, the gains in this case is only the amount of variation with respect to a predetermined state of the obstacle. Then, the obstacle determination unit 49 returns the processing to the beginning of SB1. The reason the intensity of the light-projecting unit 13 is reduced to half the normal level is that, since, when the intensity of the light-projecting unit 13 is at the normal level, the output value A40 of the first light-receiving unit 14a, the output value A50 of the second light-receiving unit 14b and the output value A150 of the third light-receiving unit 14c may be saturated for an obstacle in SB2 and SB5, it is intended to reduce the output values A40, A50 and A150 to a non-saturated level.

Then, if the repeat count m updated again in SB3 exceeds 10 (SB4, Yes), or if the output value A40 of the first light-receiving unit 14a satisfies A40>133 within 5 seconds after the first light-receiving unit 14a receives detection light (SB5, Yes), it is determined that an obstacle surely exists in the monitored area. Then, since the intensity of the light-projecting unit 13 has been varied by the light projection current varying unit 42 in the first processing of SB6 (SB6, Yes), the correction unit 43 reduces the bit values of the output value A40 of the first light-receiving unit 14a, the output value A50 of the second light-receiving unit 14b and the output value A150 of the third light-receiving unit 14c to a quarter (SB8). The reason the bit values of the output value A40 of the first light-receiving unit 14a, the output value A50 of the second light-receiving unit 14b and the output value A150 of the third light-receiving unit 14c are reduced to a quarter is that it is intended to reduce noise due to the obstacle included in the output value A40 of the first light-receiving unit 14a, the output value A50 of the second light-receiving unit 14b and the output value A150 of the third light-receiving unit 14c.

On the other hand, if the output value A40 of the first light-receiving unit 14a does not satisfy A40>133 within 5 seconds after the first light-receiving unit 14a receives detection light (SB5, No), it is determined that no obstacle exists in the monitored area. Then, the fire determination unit 48 decides to perform the determination based on the non-corrected output value of the output value A40 of the first light-receiving unit 14a with respect to a threshold set by the threshold setting unit 45 (SB9) and returns the processing to the beginning of SB1.

(Effect)

Thus, according to the embodiment, the smoke type determination unit 47 determines the type of smoke based on the output values output from the first light-receiving unit 14a, the second light-receiving unit 14b and the third light-receiving unit 14c placed at different locations with respect to one light-projecting unit 13, the output values being output in response to the detection light scattered in the monitored area. So, the first light-receiving unit 14a, the second light-receiving unit 14b and the third light-receiving unit 14c receive the detection light from the light-projecting unit 13 at the same timing, which allows determining the type of smoke based on the output values output from the first light-receiving unit 14a, the second light-receiving unit 14b and the third light-receiving unit 14c in response to the same smoke generated in the monitored area, thereby achieving accurate determination of the type of smoke.

Furthermore, the smoke type determination unit 47 determines the type of smoke based on the ratios between the output values output from the first light-receiving unit 14a, the second light-receiving unit 14b and the third light-receiving unit 14c, which allows determining whether smoke has been generated by a flaming fire or a smoking fire, not depending on the magnitude of the output values output from the first light-receiving unit 14a, the second light-receiving unit 14b and the third light-receiving unit 14c, thereby achieving further accurate determination of the type of smoke.

Furthermore, the smoke type determination unit 47 determines whether or not the type of smoke is to be determined, based on the output value A40 of the first light-receiving unit 14a having the light-receiving axis at the smallest angle with the light-projecting axis of the light-projecting unit 13, of the first light-receiving unit 14a, the second light-receiving unit 14b and the third light-receiving unit 14c, which allows determining whether or not the type of smoke is to be determined, using the first light-receiving unit 14a that can precisely detect smoke even when the detection light is not likely to be scattered by the smoke, thereby achieving accurate and quick determination of the type of smoke.

Furthermore, the fire determination unit 48 determines whether or not a fire has occurred, based on the output value A40 of the first light-receiving unit 14a having the light-receiving axis at the smallest angle with the light-projecting axis of the light-projecting unit 13, of the first light-receiving unit 14a, the second light-receiving unit 14b and the third light-receiving unit 14c, which allows determining whether or not a fire has occurred, using the first light-receiving unit 14a that can precisely detect smoke even when the detection light is not likely to be scattered by the smoke, thereby achieving accurate and quick detection of a fire.

Furthermore, when the smoke type determination unit 47 determines the type of smoke to be that of smoke generated by a flaming fire, the fire determination unit 48 corrects the output value A40 of the first light-receiving unit 14a, which allows correcting the output value A40 of the first light-receiving unit 14a depending on the characteristic for each type of smoke, thereby achieving further accurate detection of a fire.

Furthermore, the obstacle determination unit 49 determines whether or not an obstacle exists, based on the output values output from the first light-receiving unit 14a, the second light-receiving unit 14b and the third light-receiving unit 14c placed at different locations with respect to one light-projecting unit 13, the output values being output in response to the detection light scattered in the monitored area, so the first light-receiving unit 14a, the second light-receiving unit 14b and the third light-receiving unit 14c receive the detection light from the light-projecting unit 13 at the same timing, which allows determining whether or not an obstacle exists, based on the output values output from the first light-receiving unit 14a, the second light-receiving unit 14b and the third light-receiving unit 14c in response to the same obstacle, thereby achieving accurate detection of an obstacle.

Furthermore, the obstacle determination unit 49 determines whether or not an obstacle exists in the monitored area, based on the total of the output values output from the first light-receiving unit 14a, the second light-receiving unit 14b and the third light-receiving unit 14c, which allows determining whether or not an obstacle exists, by aggregating the output values output from the first light-receiving unit 14a, the second light-receiving unit 14b and the third light-receiving unit 14c, thereby achieving further accurate detection of an obstacle.

Furthermore, the obstacle determination unit 49 determines whether or not an obstacle exists, based on the output value A40 of the first light-receiving unit 14a having the light-receiving axis at the smallest angle with the light-projecting axis of the light-projecting unit 13, of the first light-receiving unit 14a, the second light-receiving unit 14b and the third light-receiving unit 14c, which allows determining whether or not an obstacle exists, using the first light-receiving unit 14a that can precisely detect an obstacle even when the detection light is not likely to be scattered by the obstacle, thereby achieving accurate and quick detection of an obstacle.

Variation of the Embodiment

While the embodiment in accordance with the invention has been described above, the specific configuration and means of the invention can be modified and improved as desired within the technical scope of the invention according to the claims. Such a variation is described below.

(Problems to be Solved and Effect of the Invention)

First, the problems to be solved by the invention and the effects of the invention are not limited to the described above, but, by the invention, a problem not described above can be solved or an effect not described above can be achieved, and also, only a portion of the problem described above may be solved or only a portion of the effect described above may be achieved.

(Separation and Merge)

Furthermore, the above-described electric components are functionally conceptual, and need not necessarily be physically configured as shown in the drawings. In other words, the specific configuration of separation and merge of the components are not limited to those shown in the drawings, but all or some of the configuration may be functionally or physically separated or merged to be configured in any unit depending on various loads and usages. For example, an analog output value may be output from the smoke sensor 1 to a receiver, and the determination of the type of smoke and the determination of the occurrence of a fire may be performed in the receiver. In order to achieve this, all or some of the control unit 40 and the storage unit 50 of the smoke sensor 1 described in the embodiment may be included in the receiver.

(Light Projection Timing Switching Unit)

In the embodiment, the light projection timing switching unit 41 can change as desired the projection timing of detection light projected by the light-projecting unit 13. For example, the light projection timing switching unit 41 may change the projection timing depending on the processing. For example, in the fire detection processing, the light projection timing switching unit 41 may change the projection timing such that the light-projecting unit 13 projects detection light for every 5 seconds until the output value A40 of the first light-receiving unit 14a falls below a predetermined value (SA1, No), and the light-projecting unit 13 projects detection light for every 2 seconds after the output value A40 of the first light-receiving unit 14a exceeds the predetermined value (SA1, Yes).

(Fire Detection Processing)

In the embodiment, the processing from SA2 to SA5 is a processing of determining the type of smoke generated by a flaming fire and the actual occurrence of the fire, the detail of which is not described here. Among these processings, the processing of SA4 was described such that the correction unit 43 triples the output value A40 of the first light-receiving unit 14a. However, the criterion for determining whether or not a fire has occurred in the monitored area may be changed based on the type of smoke determined by the smoke type determination unit 47.

Figure 10:
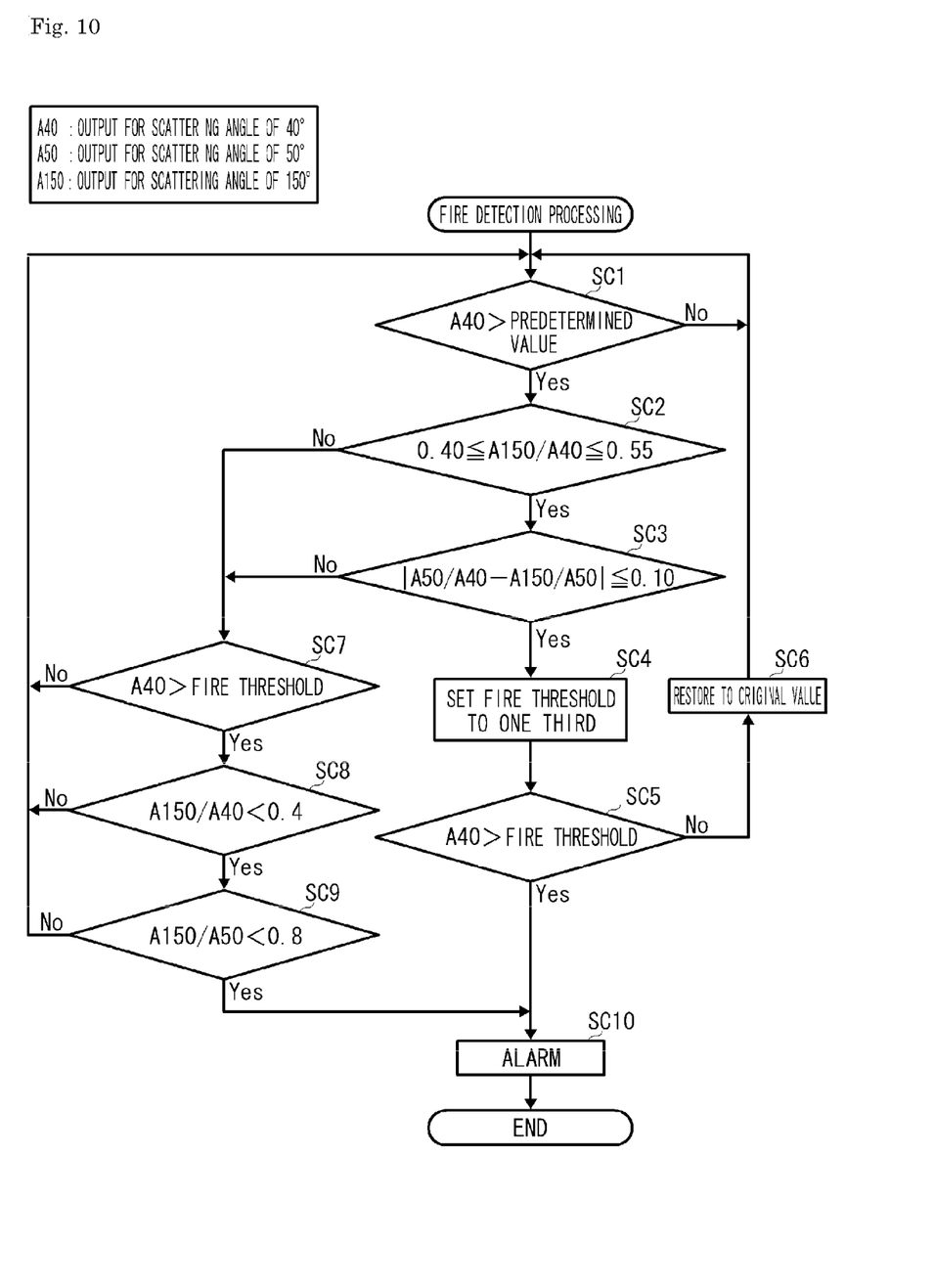
FIG. 10 is a flowchart of the fire detection processing according to a variation.

For example, FIG. 10 is a flowchart of the fire detection processing according to the variation. In this processing, the processing from SC2 to SC5 shown in FIG. 10 is the same as the processing from SA2 to SA5 shown in FIG. 8, and so is not described here. In the processing of SC4, the threshold setting unit 45 may set the threshold for determining the output value A40 of the first light-receiving unit 14a to one third. Or the threshold setting unit 45 may separately set the threshold for the processing of SC5 and the threshold for the processing of SC7 in place of the processing of SC4.

Note that the steps in the processings shown in FIGS. 8 to 10 may be modified in any appropriate way unless otherwise stated. For example, in the processing in FIG. 8, the type of smoke generated by a flaming fire is determined in SA7 and SA8 before the actual occurrence of the fire is determined in SA9. However, as in the processing in FIG. 10, the actual occurrence of a fire may be determined in the processing of SA7, and then the type of smoke generated by a flaming fire may be determined in the processing of SC8 and SC9.

DESCRIPTION OF REFERENCE NUMERALS AND SIGNS 1 smoke sensor
10 sensor body
11 holder
11a, 11b, 11c, 11d opening
11e transparent cover
12 circuit board
13 light-projecting unit
14 light-receiving unit
14a first light-receiving unit
14b second light-receiving unit
14c third light-receiving unit
15 detection space
20 light-projecting unit driver circuit
21 first light-receiving unit amplifier circuit
22 second light-receiving unit amplifier circuit
23 third light-receiving unit amplifier circuit
30 oscillation unit
40 control unit
41 light projection timing switching unit
42 light projection current varying unit
43 correction unit
44 calculation unit
45 threshold setting unit 46 gain adjustment unit
47 smoke type determination unit
48 fire determination unit
49 obstacle determination unit
50 storage unit

The invention claimed is:

1. A smoke sensing system comprising:
a light-projecting means for projecting detection light toward a monitored area;
a plurality of light-receiving means for receiving the detection light scattered by particles existing in the monitored area at the same timing, the plurality of light-receiving means being arranged such that the angles between the light-receiving axes of the plurality of light-receiving means and the light-projecting axis of the light-projecting means are different from one another;
a smoke type determining means for determining a type of smoke generated in the monitored area based on output values output from the plurality of light-receiving means; and
a fire determining means for determining whether or not a fire has occurred in the monitored area, based on the output values output from the plurality of light-receiving means; and
an obstacle determining means for determining whether or not an obstacle exists in the monitored area, based on the output values output from the plurality of light-receiving means,
wherein the smoke type determining means determines the type of smoke generated in the monitored area based on a ratio between the output values output from the plurality of light-receiving means and,
wherein the obstacle determining means determines whether or not an obstacle exists in the monitored area, based on the total of the output values output from the plurality of light-receiving means.

2. The smoke sensing system according to claim 1, wherein the smoke type determining means determines whether or not the type of smoke generated in the monitored area is to be determined, based on the output value from a light-receiving means with the largest output value of the plurality of light-receiving means.

3. The smoke sensing system according to claim 1, wherein the fire determining means determines whether or not a fire has occurred in the monitored area, based on the output value from a light-receiving means with the largest output value of the plurality of light-receiving means.

4. The smoke sensing system according to claim 1, wherein the smoke type determining means determines whether or not the type of smoke generated in the monitored area is to be determined, based on the output value from a light-receiving means having the light-receiving axis at the smallest angle with the light-projecting axis of the light-projecting means, of the plurality of light-receiving means.

5. The smoke sensing system according to claim 1, wherein the fire determining means determines whether or not a fire has occurred in the monitored area, based on the output value from a light-receiving means having the light-receiving axis at the smallest angle with the light-projecting axis of the light-projecting means, of the plurality of light-receiving means.

6. The smoke sensing system according to claim 1, wherein the fire determining means changes the criterion for determining whether or not a fire has occurred in the monitored area, based on the type of the smoke determined by the smoke type determining means.

7. The smoke sensing system according to claim 1, wherein the fire determining means corrects the output value output from the light-receiving means, based on the type of the smoke determined by the smoke type determining means.

8. The smoke sensing system according to claim 1, wherein the obstacle determining means determines whether or not an obstacle exists in the monitored area, based on the output value from a light-receiving means with the largest output value of the plurality of light-receiving means.

9. The smoke sensing system according to claim 1, wherein the obstacle determining means determines whether or not an obstacle exists in the monitored area, based on the output value from a light-receiving means having the light-receiving axis at the smallest angle with the light-projecting axis of the light-projecting means, of the plurality of light-receiving means.

10. The smoke sensing system according to claim 1, wherein the angle between the light-receiving axis of at least one of the plurality of light-receiving means and the light-projecting axis of the light-projecting means is within a range from 150° to 160°.

11. A smoke sensor comprising:
a light-projecting means for projecting detection light toward a monitored area;
a plurality of light-receiving means for receiving the detection light scattered by particles existing in the monitored area at the same timing, the plurality of light-receiving means being arranged such that the angles between the light-receiving axes of the plurality of light-receiving means and the light-projecting axis of the light-projecting means are different from one another;
a smoke type determining means for determining a type of smoke generated in the monitored area based on output values output from the plurality of light-receiving means; and
a fire determining means for determining whether or not a fire has occurred in the monitored area, based on the output values output from the plurality of light-receiving means; and
an obstacle determining means for determining whether or not an obstacle exists in the monitored area, based on the output values output from the plurality of light-receiving means,
wherein the smoke type determining means determines the type of smoke generated in the monitored area based on a ratio between the output values output from the plurality of light-receiving means and,
wherein the obstacle determining means determines whether or not an obstacle exists in the monitored area, based on the total of the output values output from the plurality of light-receiving means.

12. A receiver for receiving an output value output from a smoke sensor, the smoke sensor comprising: a light-projecting means for projecting detection light toward a monitored area at the same timing; and a plurality of light-receiving means for receiving the detection light scattered by particles existing in the monitored area, the receiver comprising:
a smoke type determining means for determining a type of smoke generated in the monitored area based on the output value received from the smoke sensor; and
a fire determining means for determining whether or not a fire has occurred in the monitored area, based on the output value received from the smoke sensor, and an obstacle determining means for determining whether or not an obstacle exists in the monitored area, based on the output values output from the plurality of light-receiving means, wherein the smoke type determining means determines the type of smoke generated in the monitored area based on a ratio between the output values output from the plurality of light-receiving means and, wherein the obstacle determining means determines whether or not an obstacle exists in the monitored area, based on the total of the output values output from the plurality of light-receiving means.

* * * * *